United States Patent
Sun et al.

(10) Patent No.: US 11,596,444 B2
(45) Date of Patent: Mar. 7, 2023

(54) AUTOMATIC RECOGNITION METHOD FOR SPATIAL POSITION AND POSE OF PARALLEL EXTERNAL FIXATOR FOR FRACTURE REDUCTION

(71) Applicant: BEIJING NATON MEDICAL TECHNOLOGY HOLDINGS CO., LTD., Beijing (CN)

(72) Inventors: Tao Sun, Tianjin (CN); Sida Liu, Tianjin (CN); Wei Yan, Tianjin (CN); Yimin Song, Tianjin (CN)

(73) Assignee: BEIJING NATON MEDICAL TECHNOLOGY HOLDINGS CO., LTD., Beijing (CN)

(*) Notice: Subject to any disclaimer, the term of this patent is extended or adjusted under 35 U.S.C. 154(b) by 157 days.

(21) Appl. No.: 16/767,100

(22) PCT Filed: Sep. 19, 2018

(86) PCT No.: PCT/CN2018/106512
§ 371 (c)(1),
(2) Date: May 26, 2020

(87) PCT Pub. No.: WO2020/029378
PCT Pub. Date: Feb. 13, 2020

(65) Prior Publication Data
US 2021/0361322 A1    Nov. 25, 2021

(30) Foreign Application Priority Data
Aug. 10, 2018    (CN) .......................... 201810909100.4

(51) Int. Cl.
*A61B 17/66*    (2006.01)
*A61B 34/10*    (2016.01)
(Continued)

(52) U.S. Cl.
CPC .............. *A61B 17/66* (2013.01); *A61B 17/62* (2013.01); *A61B 34/10* (2016.02); *A61B 90/37* (2016.02);
(Continued)

(58) Field of Classification Search
CPC ......... A61B 17/60; A61B 17/62; A61B 17/64; A61B 17/645; A61B 17/66; A61B 34/10
See application file for complete search history.

(56) References Cited

U.S. PATENT DOCUMENTS

2011/0313418 A1* 12/2011 Nikonovas ............. A61B 17/66
606/56
2014/0379038 A1* 12/2014 Dogramadzi .......... A61B 17/66
606/86 R
(Continued)

FOREIGN PATENT DOCUMENTS

CN        2590538 Y      12/2003
CN      101002696 A       7/2007
(Continued)

OTHER PUBLICATIONS

International Search Report of PCT/CN2018/106512.
Written Opinion of PCT/CN2018/106512.

*Primary Examiner* — Julianna N Harvey
(74) *Attorney, Agent, or Firm* — Hodgson Russ LLP

(57) ABSTRACT

The present invention discloses an automatic recognition method for spatial position and pose of parallel external fixator, including the following steps of: installing three markers on each of the two fixation rings of the parallel external fixator; obtaining 3D images of six marker balls after scanning and reconstruction by a common 3D clinical imaging system; recognizing the sphere center coordinates of the six marker balls by sphere fitting algorithm; according to the mounting configuration of the markers on the two fixation rings, establishing coordinate systems of two fixa- (Continued)

tion rings and determining the spatial position and pose of the external fixator; in addition, by obtaining the 3D images of the fracture bone segments with the 3D clinical imaging system and simulating the movement of the fracture deformity correction, the adjustment schedule of the external fixator struts can be achieved.

8 Claims, 4 Drawing Sheets

(51) Int. Cl.
    *A61B 90/00*     (2016.01)
    *A61B 17/62*     (2006.01)

(52) U.S. Cl.
    CPC ........ *A61B 90/39* (2016.02); *A61B 2090/376* (2016.02); *A61B 2090/3983* (2016.02)

(56) References Cited

U.S. PATENT DOCUMENTS

| 2016/0042571 | A1* | 2/2016 | Mikheev | G06T 19/20 345/419 |
| 2018/0055569 | A1* | 3/2018 | Wahl | A61B 34/10 |

FOREIGN PATENT DOCUMENTS

| CN | 203425022 U | 2/2014 |
| CN | 104398295 A | 3/2015 |
| CN | 106859750 A | 6/2017 |
| CN | 206534699 U | 10/2017 |
| WO | 2017213425 A1 | 12/2017 |

* cited by examiner

AUTOMATIC RECOGNITION METHOD FOR SPATIAL POSITION AND POSE OF PARALLEL EXTERNAL FIXATOR FOR FRACTURE REDUCTION

CROSS-REFERENCE TO RELATED APPLICATIONS

This application is a national stage application of PCT Application No. PCT/CN2018/106512. This application claims priority from PCT Application No. PCT/CN2018/106512, filed Sep. 19, 2018, CN Application No. CN 201810909100.4, filed Aug. 10, 2018, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference was individually incorporated by reference.

FIELD OF THE INVENTION

The present invention relates to the field of orthopedic external fixation, in particular to an automatic recognition method for spatial position and pose of parallel external fixator based on three-dimensional clinical image, in the use of fracture reduction treatment.

BACKGROUND OF THE INVENTION

The existing parallel external fixator usually comprises a pair of fixation rings fixedly connected to the fractured bone and six struts connected to the fixation rings. The parallel external fixator can not only stably fix the fracture segment, but also adjust the fracture segment and achieve more accurate fracture reduction by adjusting the relative position and pose of the fixation rings. In addition, the parallel external fixator can also be used for bone deformity correction after osteotomy treatment. Due to the individuality of the fracture condition and the clinical fixator installation of the patient, it is necessary to determine the position and pose of the parallel external fixator before applying it for fracture reduction or deformity correction, and then plan the adjustment schedule according to the measured position and pose. The position and pose information of the parallel external fixator includes spatial position and pose of the external fixator structure and the fractured bone segment relative to the external fixator. How to determine the spatial position and pose information of the external fixator through the clinical information is a major difficulty in the application of parallel external fixator.

U.S. Pat. No. 9,204,937 and EP2767252 provide two similar methods for determining the position and pose of the parallel external fixator, mainly including: taking X-ray anteroposterior and lateral radiographs of the fractured bone containing the complete parallel external fixator; manually measuring the position and pose parameters between the fracture segments, and the installation parameters between the fractured bone and the external fixator on the X-ray image; reading the length of the fixator struts and measuring the axial rotation angle of the limb relative to the fixator in clinic; solving the position and pose of the parallel external fixator and the fractured bone by using the above parameters. The method provided by the above patents has the following problems: requiring extensive manual measurement operations, existing subjective and objective errors, the adopted X-ray image does not contain the axial rotation between the bone segment and the external fixator; thus resulting in low efficiency of the clinical application of the parallel external fixator, and inconsistence between the bone adjustment accuracy and the mechanical accuracy of the fixator structure.

Therefore, a heretofore unaddressed need exists in the art to address the aforementioned deficiencies and inadequacies.

SUMMARY OF THE INVENTION

The purpose of the present invention is to overcome the disadvantages of the prior art, provide an automatic recognition method for spatial position and pose of parallel external fixator, which represent the spatial configuration of the external fixator and connected fractured bone segments.

The technical scheme of the present invention is as follows.

An automatic recognition method for spatial position and pose of parallel external fixator, including the following steps of:

(1) installing markers, including: defining two fixation rings of the parallel external fixator as a proximal fixation ring and a distal fixation ring; installing three markers on the proximal fixation ring and three on the distal fixation ring; wherein the six markers have the same structure and respectively comprise a marker ball and a marker pin shaft; the distance from the sphere center of each marker on the proximal fixation ring to the upper surface of the proximal fixation ring is a fixed value $h_M$; the distance from the sphere center of each marker on the distal fixation ring to the upper surface of the distal fixation ring is the same fixed value $h_M$; the marker balls and the marker pin shafts are made of different materials, so that the marker balls can be recognized by a common three-dimensional (hereinafter referred to as 3D) clinical imaging system, and the marker pin shafts will not be recognized;

(2) acquiring 3D images, including: 3D scanning the fracture site and the parallel external fixator with installed markers, performing threshold division and 3D reconstruction to obtain 3D images of a proximal bone segment, a distal bone segment and six marker balls; storing the data of the 3D images in the computer system by using a 3D point cloud format; the 3D point cloud format is composed of a plurality of data points to describe the surface shape of a 3D object;

(3) sphere fitting the marker balls, including:

(3a) based on the 3D point cloud data of the six marker balls and the known diameter of the marker balls, fitting the 3D point cloud of the six marker balls into six spheres by a certain sphere fitting algorithm;

(3b) by referring to 3D images of the proximal bone segment and the distal bone segment, specifying the correspondence relationship between six marker balls in the 3D images and the six markers on the parallel external fixator, and then storing it into the computer system;

(4) specifying installation information of the markers, including:

(4a) establishing a proximal coordinate system p-uvw attached to the proximal fixation ring and a distal coordinate system P-UVW attached to the distal fixation ring;

(4b) according to the actual mounting configuration among a first marker, a second marker, a third marker and the proximal fixation ring, by using the structural dimensions of the proximal fixation ring, calculating the coordinates of the first sphere center of the first marker ball $M_1(u_1v_1w_1)$, the second sphere center of the second marker ball $M_2(u_2v_2w_2)$, and the third sphere center of the third marker ball $M_3(u_3v_3w_3)$ in the proximal coordinate system p-uvw, respectively; and by using the data of the distal fixation ring, calculating to obtain the coordinates of the fourth sphere center of the fourth marker ball $M_4(U_4V_4W_4)$, the fifth sphere center of the fifth marker ball $M_5(U_5V_5W_5)$, and the sixth sphere center of the sixth marker ball $M_6(U_6V_6W_6)$ in the distal coordinate system P-UVW, respectively; the sphere center coordinates of the six marker balls constitute the markers installation information of the external fixator;

(4c) inputting the markers installation information into a computer system;

(5) recognizing spatial position and pose of the coordinate systems, including:

(5a) according to the plane formed by the first sphere center, second sphere center and third sphere center is parallel to the upper surface of the proximal fixation ring, calculating a normal vector $\vec{pw}$ of the upper surface of the proximal fixation ring by the following formula, which corresponds to the axis w of the proximal coordinate system p-uvw:

$$\vec{pw} = \frac{\overrightarrow{M_1M_2} \times \overrightarrow{M_2M_3}}{|\overrightarrow{M_1M_2} \times \overrightarrow{M_2M_3}|}$$

in which, $\overrightarrow{M_1M_2}$ is a vector pointing from the first sphere center to the second sphere center in the point cloud reference coordinate system O-xyz, and $\overrightarrow{M_1M_2}=(x_{M2}-x_{M1}, y_{M2}-y_{M1}, z_{M2}-z_{M1})$; $\overrightarrow{M_2M_3}$ is a vector pointing from the second sphere center to the third sphere center in the point cloud reference coordinate system O-xyz, and $\overrightarrow{M_2M_3}=(x_{M3}-x_{M2}, y_{M3}-y_{M2}, z_{M3}-z_{M2})$;

(5b) assuming the coordinates of the origin p of the proximal coordinate system p-uvw be $p_{O-xyz}=(x_{pO}, y_{pO}, z_{pO})$ in the point cloud reference coordinate system O-xyz, according to the coordinates $M_1(u_1v_1w_1)$, $M_2(u_2v_2w_2)$ and $M_3(u_3v_3w_3)$ obtained by the step (4b) in the proximal coordinate system p-uvw, calculating the coordinates of the origin p in the point cloud reference coordinate system O-xyz by solving the following distance equations:

$$\begin{cases} |\overrightarrow{pM_1}|^2 = u_1^2 + v_1^2 + w_1^2 \\ |\overrightarrow{pM_2}|^2 = u_2^2 + v_2^2 + w_2^2 \\ |\overrightarrow{pM_3}|^2 = u_3^2 + v_3^2 + w_3^2 \end{cases}$$

(5c) in the point cloud reference coordinate system O-xyz, assuming the value of unit vector $\vec{pu}$ of the proximal coordinate system p-uvw be $\vec{pu}=(x_{pu}, y_{pu}, z_{pu})$; respectively taking the scalar products of vectors $\overrightarrow{pM_1}$, $\overrightarrow{pM_2}$ and $\overrightarrow{pM_3}$ of the first sphere center, the second sphere center and the third sphere center with the unit vector $\vec{pu}$, the outcomes are equivalent to the components $u_1$, $u_2$ and $u_3$ of the first sphere center, the second sphere center and the third sphere center along the axis $\vec{pu}$, as the following equations:

$$\begin{cases} \overrightarrow{pM_1} \cdot \vec{pu} = u_1 \\ \overrightarrow{pM_2} \cdot \vec{pu} = u_2 \\ \overrightarrow{pM_3} \cdot \vec{pu} = u_3 \end{cases}$$

in which, the vectors $\overrightarrow{pM_1}$, $\overrightarrow{pM_2}$ and $\overrightarrow{pM_3}$ are determined by $\overrightarrow{pM_1}=(x_{M1}-x_{pO}, y_{M1}-y_{pO}, z_{M1}-z_{pO})$, $\overrightarrow{pM_2}=(x_{M2}-x_{pO}, y_{M2}-y_{pO}, z_{M2}-z_{pO})$ and $\overrightarrow{pM_3}=(x_{M3}-x_{pO}, y_{M3}-y_{pO}, z_{M3}-z_{pO})$, respectively; solving the above equation set to determine the value of unit vector $\vec{pu}$ of the proximal coordinate system p-uvw;

(5d) calculating the unit vector $\vec{pv}$ of the proximal coordinate system p-uvw by using the right-hand rule, taking the following equation:

$$\vec{pv} = \vec{pw} \times \vec{pu}$$

(5e) repeating step (5a) to step (5d), according to the coordinates of the fourth sphere center $M_4(U_4V_4W_4)$, the fifth sphere center $M_5(U_5V_5W_5)$ and the sixth sphere center $M_6(U_6V_6W_6)$ in the distal coordinate system P-UVW, determining the coordinate of the origin P of the distal coordinate system P-UVW in the point cloud reference coordinate system O-xyz be $P_{O-xyz}=(x_{PO}, y_{PO}, z_{PO})$, and determining the value of unit vectors $\overrightarrow{PU}$, $\overrightarrow{PV}$ and $\overrightarrow{PW}$ of the three coordinates axes of the distal coordinate system P-UVW in the point cloud reference coordinate system O-xyz;

(5f) determining the position and pose of the proximal coordinate system p-uvw relative to the point cloud reference coordinate system O-xyz by using the origin coordinate $p_{O-xyz}$ and the unit vectors $\vec{pu}$, $\vec{pv}$, $\vec{pw}$; determining the position and pose of the distal coordinate system P-UVW relative to the point cloud reference coordinate system O-xyz by using the origin coordinate $P_{O-xyz}$ and the unit vectors $\overrightarrow{PU}$, $\overrightarrow{PV}$, $\overrightarrow{PW}$; and storing the spatial position and pose of the proximal and distal coordinate systems into the computer system;

(6) determining the spatial position and pose of the external fixator, including: (6a) calculating the relative position of the proximal fixation ring and the distal fixation ring by using the origin coordinate $p_{O-xyz}$ of proximal coordinate system and the origin coordinate $P_{O-xyz}$ of distal coordinate system, and expressing the relative position with a position vector $\vec{r}_{P_p}$ as the following:

$$\vec{r}_{P_p} = p_{O-xyz} - P_{O-xyz} = (x_{pO}-x_{PO}, y_{pO}-y_{PO}, z_{pO}-z_{PO})$$

(6b) calculating the relative pose of the proximal fixation ring and the distal fixation ring by using the unit vectors $\vec{pu}$, $\vec{pv}$, $\vec{pw}$ of proximal coordinate system and $\overrightarrow{PU}$, $\overrightarrow{PV}$, $\overrightarrow{PW}$ of distal coordinate system, and express the relative pose with a pose matrix $R_P^p$ as the following:

$$R_P^p = \begin{bmatrix} \vec{pu} \cdot \vec{PU} & \vec{pv} \cdot \vec{PU} & \vec{pw} \cdot \vec{PU} \\ \vec{pu} \cdot \vec{PV} & \vec{pv} \cdot \vec{PV} & \vec{pw} \cdot \vec{PV} \\ \vec{pu} \cdot \vec{PW} & \vec{pv} \cdot \vec{PW} & \vec{pw} \cdot \vec{PW} \end{bmatrix}$$

(6c) determining the spatial position and pose of the external fixator according to the position vector $\vec{r}_{P_p}$ and pose matrix $R_P^p$ of the proximal fixation ring relative to the distal fixation ring;

(7) determining the adjustment values of the external fixator for fracture reduction, including:

displaying the 3D images of the proximal bone segment and the distal bone segment on the screen of the computer system, moving the 3D images displayed on the screen according to the desired fracture reduction movement, achieving the correct alignment of the proximal bone segment and the distal bone segment in the screen display; automatically calculating and storing, by the computer system, the translation and rotation movement values of the proximal bone segment 3D image relative to the distal bone segment 3D image in the point cloud reference coordinate system O-xyz during the reduction, wherein the translation and rotation movement values of the proximal bone segment 3D image relative to the distal bone segment 3D image are equal to the translation and rotation adjustment values of the proximal fixation ring relative to the distal fixation ring during the reduction, thus the adjustment values of the external fixator for fracture reduction is determined;

(8) according to the recognized spatial position and pose of the external fixator, the adjustment values of the external fixator for fracture reduction, and by using a certain kinematics algorithm in the field of robotics, the adjustment schedule of the external fixator struts for fracture reduction is obtained; adjusting the external fixator struts referring to the adjustment schedule, the fracture reduction is achieved.

The present invention has following advantages: the method of the present invention is simple and reliable by avoiding manual measurement operation, and the method only needs to input some known structural data; the present invention adopts a 3D clinical imaging system as the source of information, which can truly and completely provide the spatial configuration of the parallel external fixator and the fractured site; the method of the present invention can effectively improve the efficiency and precision of the parallel external fixator in clinical application.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION OF THE EMBODIMENTS

Figure 1:
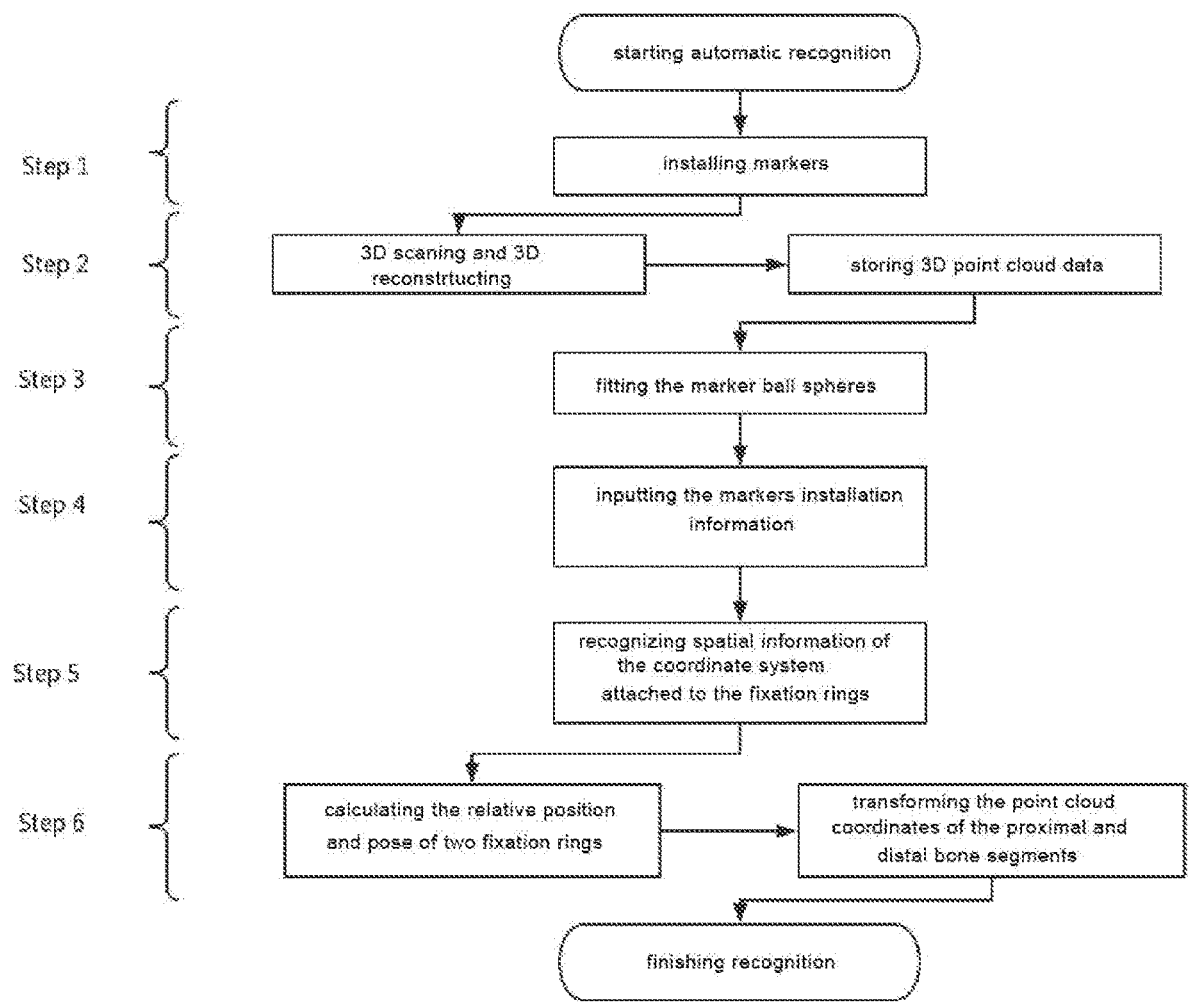
FIG. 1 is a flow diagram of an automatic recognition method for spatial position and pose of parallel external fixator for fracture reduction according to the present invention.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout.

The embodiments of the present invention will be described below in detail with reference to the drawings.

Figure 2:
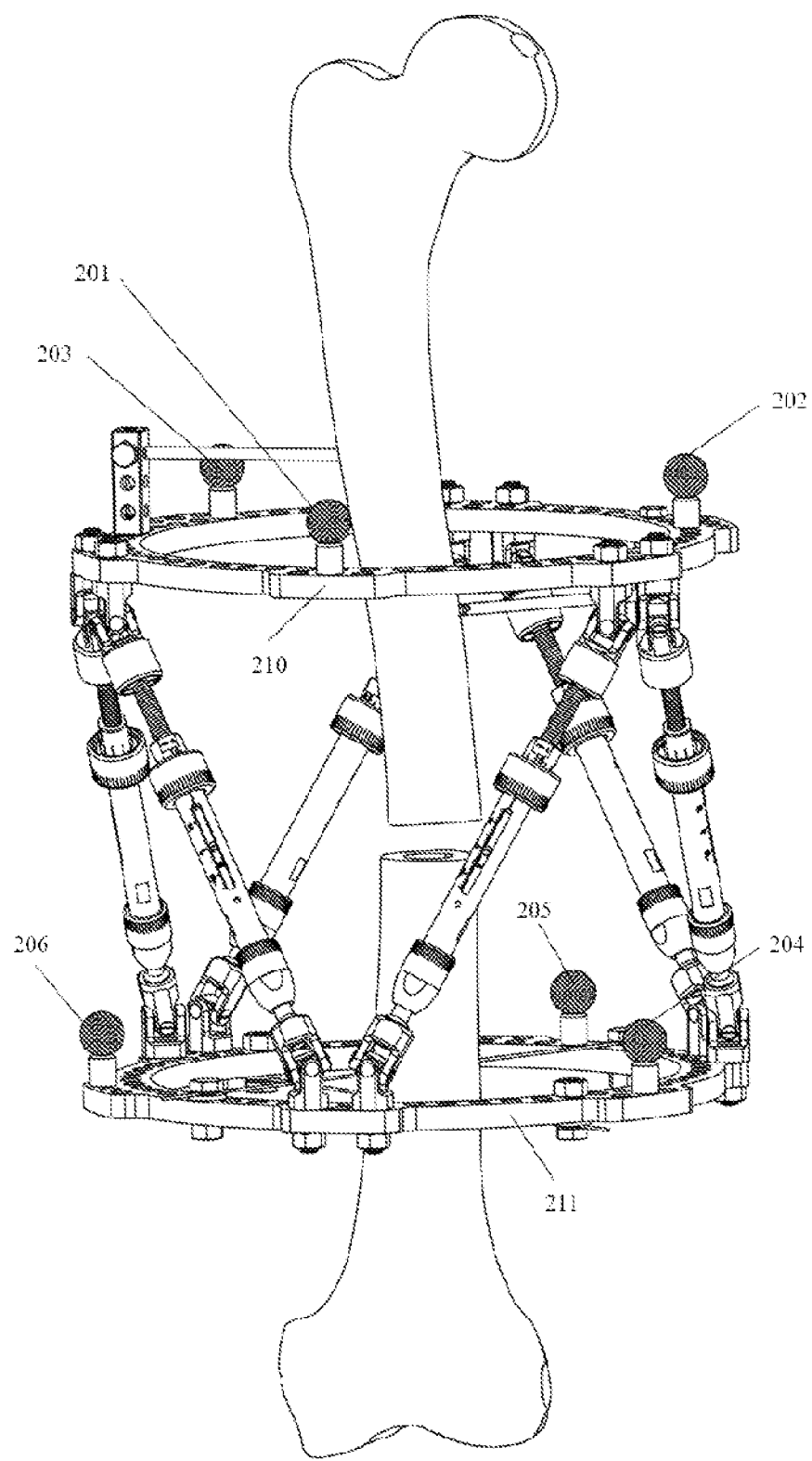
FIG. 2 is a schematic view showing the parallel external fixator mounted with markers according to the present invention.

As shown in FIG. 1, an automatic recognition method for spatial position and pose of parallel external fixator, including the following steps of:

(1) installing markers, including: defining two fixation rings of the parallel external fixator as a proximal fixation ring 210 and a distal fixation ring 211; installing three markers on the proximal fixation ring 210 and three on the distal fixation ring 211; wherein the six markers is defined as a first marker 201, a second marker 202, a third marker 203, a fourth marker 204, a fifth marker 205 and a sixth marker 206 in order (see FIG. 2). Preferably, the first, second and third markers 201, 202, 203 are arranged as far as possible from each other; the fourth, fifth and sixth markers 204, 205, 206 are arranged as far as possible from each other, which can effectively improve the recognition precision of the method provided by the present invention. The six markers have the same structure and each comprise a marker ball and a marker pin shaft. After installed the first, second and third markers 201, 202 and 203, the distance from the each sphere center of the first, second and third markers to the upper surface of the proximal fixation ring 210 is a fixed value $h_M$; after installed the fourth, fifth and the sixth markers 204, 205 and 206, the distance from the each sphere center of the fourth, fifth and the sixth markers to the upper surface of the distal fixation ring 211 is the same fixed value $h_M$. The marker balls and the marker pin shafts are made of different materials, so that the marker balls can be recognized by a common 3D clinical imaging system, and the marker pin shafts will not be recognized; preferably, the marker balls can be made of metal materials such as stainless steel or aluminum alloy, and the marker pin shafts can be made of plastic materials such as ABS or PE.

Figure 3:
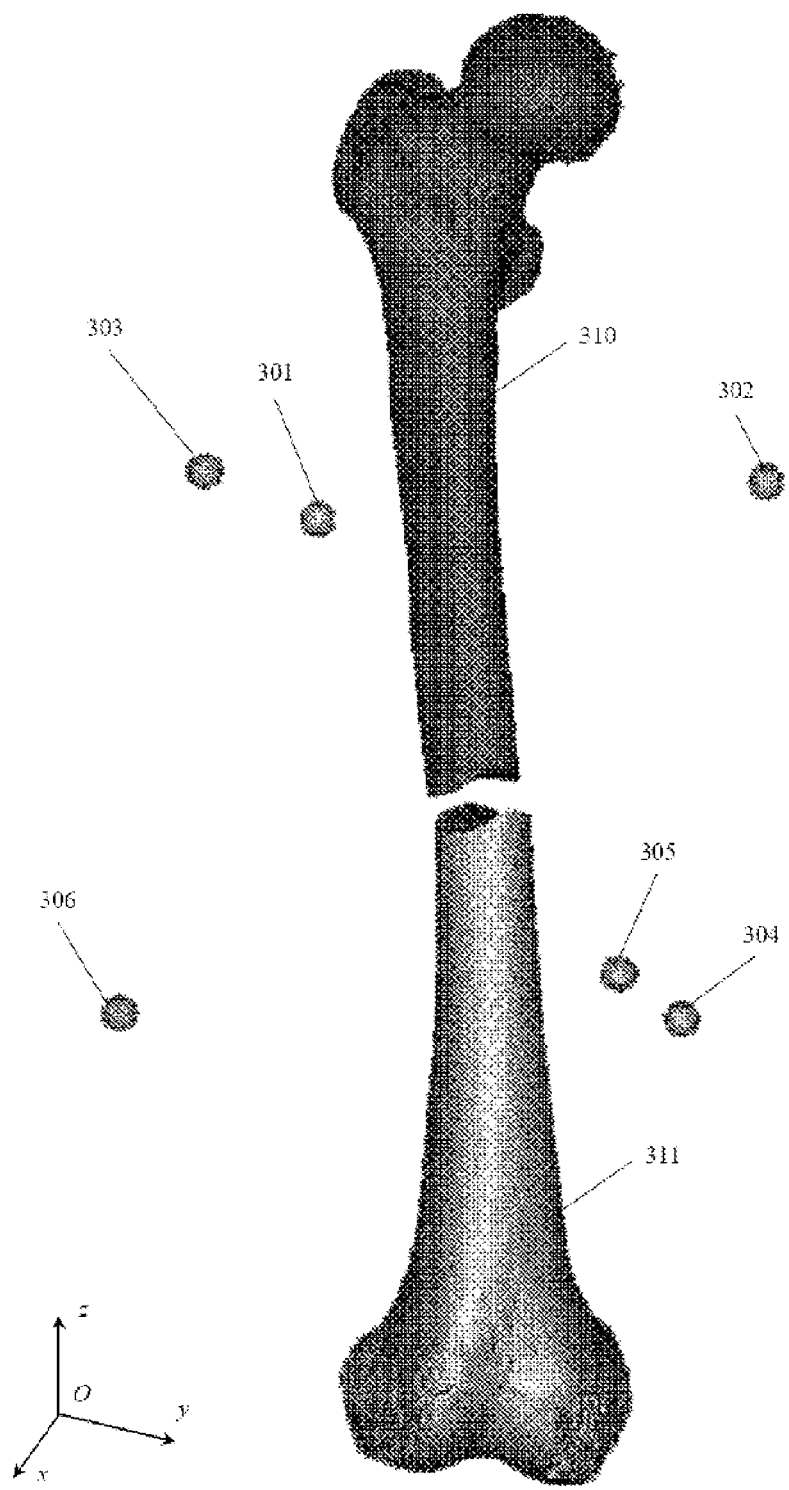
FIG. 3 is a 3D image of the fractured bone segments and markers shown in FIG. 1 acquired by 3D clinical image scan and reconstruction.

(2) Acquiring 3D images, including: 3D scanning the fracture site and the parallel external fixator with installed markers, performing threshold division and 3D reconstruction to obtain 3D images of a proximal bone segment 310, a distal bone segment 311 and six marker balls 301, 302, 303, 304, 305, 306 (see FIG. 3); storing the data of the 3D images in the computer system by using a 3D point cloud format; the 3D point cloud format is composed of a plurality of data points to describe the surface shape of a 3D object. Preferably, a STL format is adopted to store the 3D image data.

(3) Sphere fitting the marker balls, including:

(3a) based on the 3D point cloud data of the six marker balls and the known diameter of the marker balls, fitting the 3D point cloud of the six marker balls into six spheres by a certain sphere fitting algorithm.

Preferably, adopting the least square method to fit the 3D point cloud of each marker ball into a sphere. Setting up a point cloud reference coordinate system O-xyz, assuming the fitted sphere center coordinates of an arbitrary $k^{th}$ marker ball in the reference coordinate system O-xyz as $(x_{Mk}, y_{Mk}, z_{Mk})$, and the distance $D_i$ from the $i^{th}$ point of the $k^{th}$ marker ball's point cloud to the fitted sphere center can be expressed as:

$$D_i^2(x_{Mk}, y_{Mk}, z_{Mk}) = (x_i - x_{Mk})^2 + (y_i - y_{Mk})^2 + (z_i - z_{Mk})^2 \quad (1)$$

in which, $x_i$, $y_i$ and $z_i$ represent the coordinates of the $i^{th}$ point of the $k^{th}$ marker ball's point cloud in the reference coordinate system O-xyz. The sum of square residual between $D_i$ and the actual marker ball radius $r_M$ is:

$$S(x_{Mk}, y_{Mk}, z_{Mk}) = \Sigma(D_i^2 - d_{Mk}^2)^2 \quad (2)$$

When the sum of square residual S reaches its minimum value, the corresponding coordinates $x_{Mk}$, $y_{Mk}$ and $z_{Mk}$ is the best fitted sphere center of the $k^{th}$ marker ball's point cloud.

(3b) By referring to the 3D images of the proximal bone segment 310 and the distal bone segment 311, specifying the corresponding relationship between six marker balls 301, 302, 303, 304, 305, 306 in the 3D images and the six markers 201, 202, 203, 204, 205, 206 on the parallel external fixator, and then storing it into the computer system.

(4) Specifying installation information of the markers, including:

(4a) establishing a proximal coordinate system p-uvw attached to the proximal fixation ring 210 and a distal coordinate system P-UVW attached to the distal fixation ring 211.

Figure 5:
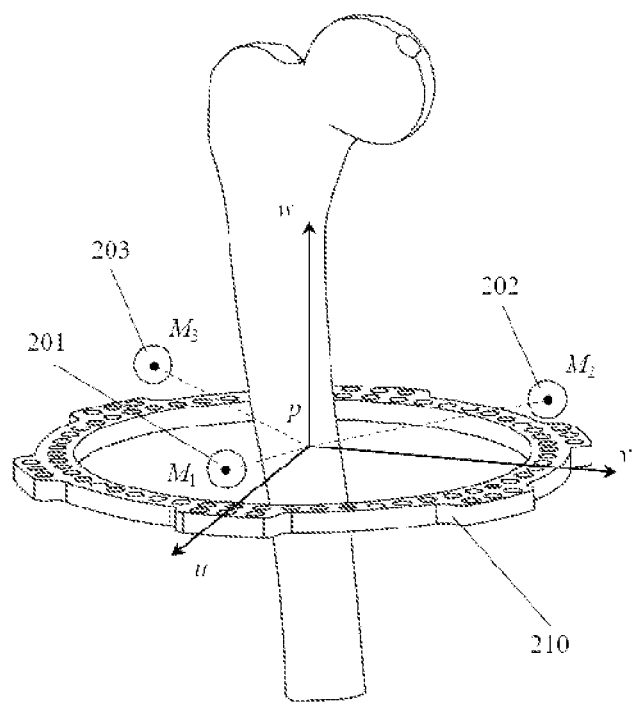
FIG. 5 is a schematic view showing the spatial positional relationship among the fourth marker, the fifth marker, and the sixth marker of the external fixator, and the distal coordinate system.
Figure 4:
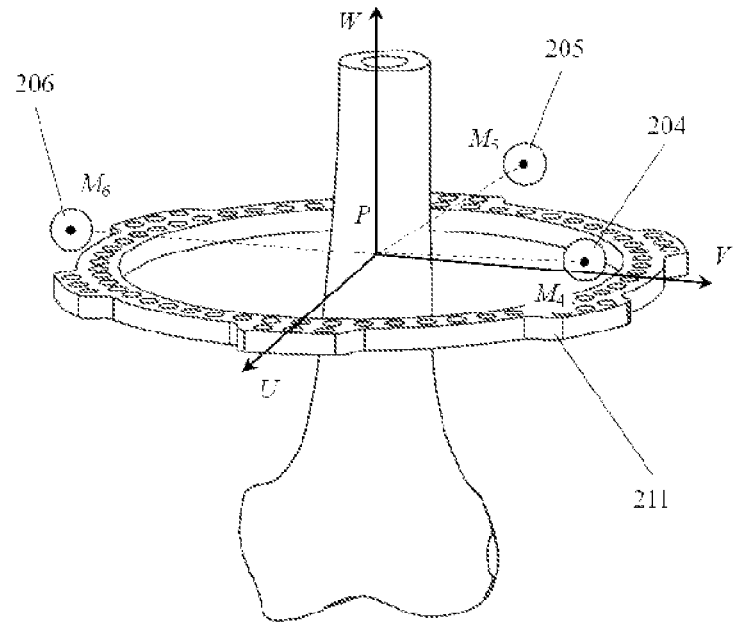
FIG. 4 is a schematic view showing the spatial positional relationship among the first marker, the second marker, and the third marker of the external fixator, and the proximal coordinate system.

(4b) According to the actual mounting configuration among the first marker 201, second marker 202, third marker 203 and proximal fixation ring 210, by using the structural dimensions of the proximal fixation ring 210, calculating to obtain the coordinates $M_1(u_1, v_1, w_1)$, $M_2(u_2, v_2, w_2)$ and $M_3(u_3, v_3, w_3)$ of the first sphere center of the first marker ball 201, the second sphere center of the second marker ball 202 and the third sphere center of the third marker ball 203 in the proximal coordinate system p-uvw, respectively (see FIG. 4); and by using the structural dimensions of the distal fixation ring 211, calculating to obtain the coordinates $M_4(U_4, V_4, W_4)$, $M_5(U_5, V_5, W_5)$ and $M_6(U_6, V_6, W_6)$ of the fourth sphere center of the fourth marker ball, the fifth sphere center of the fifth marker ball and the sixth sphere center of the sixth marker ball in the distal coordinate system P-UVW, respectively (see FIG. 5). The sphere center coordinates of the six marker balls 301, 302, 303, 304, 305, 306 constitute the markers installation information of the external fixator.

(4c) Inputting the markers installation information into the computer system.

(5) Recognizing spatial position and pose information of the coordinate system, including:

(5a) According to the plane formed by first sphere center, second sphere center and the third sphere center is parallel to the upper surface of the proximal fixation ring 210, calculating a normal vector $\vec{pw}$ of the upper surface of the proximal fixation ring 210 by the following formula, which corresponds to the axis w of the proximal coordinate system p-uvw:

$$\vec{pw} = \frac{\vec{M_1M_2} \times \vec{M_2M_3}}{|\vec{M_1M_2} \times \vec{M_2M_3}|} \quad (3)$$

in which, $\vec{M_1M_2}$ is a vector pointing from the first sphere center to the second sphere center in the point cloud reference coordinate system O-xyz, and $\vec{M_1M_2} = (x_{M2} - x_{M1}, y_{M2} - y_{M1}, z_{M2} - z_{M1})$; $\vec{M_2M_3}$ is a vector pointing from the second sphere center to the third sphere center in the point cloud reference coordinate system O-xyz, and $\vec{M_2M_3} = (x_{M3} - x_{M2}, y_{M3} - y_{M2}, z_{M3} - z_{M2})$.

(5b) Assuming the coordinates of the origin p of the proximal coordinate system p-uvw be $p_{O-xyz} = (x_{pO}, y_{pO}, z_{pO})$ in the point cloud reference coordinate system O-xyz, according to the coordinates $M_1(u_1, v_1, w_1)$, $M_2(u_2, v_2, w_2)$ and $M_3(u_3, v_3, w_3)$ obtained by the step (4b) in the proximal coordinate system p-uvw, calculating the coordinates of the origin p in the point cloud reference coordinate system O-xyz by solving the following distance equations:

$$\begin{cases} |\vec{pM_1}|^2 = u_1^2 + v_1^2 + w_1^2 \\ |\vec{pM_2}|^2 = u_2^2 + v_2^2 + w_2^2 \\ |\vec{pM_3}|^2 = u_3^2 + v_3^2 + w_3^2 \end{cases} \quad (4)$$

(5c) In the point cloud reference coordinate system O-xyz, assuming the value of unit vector $\vec{pu}$ of the proximal coordinate system p-uvw be $\vec{pu} = (x_{pu}, y_{pu}, z_{pu})$; respectively taking the scalar products of vectors $\vec{pM_1}$, $\vec{pM_2}$ and $\vec{pM_3}$ of the first sphere center, the second sphere center and the third sphere center with the unit vector $\vec{pu}$, the outcomes are equivalent to the vector components $u_1$, $u_2$ and $u_3$ of the first sphere center, the second sphere center and the third sphere center along the axis $\vec{pu}$, expressing as the following:

$$\begin{cases} \vec{pM_1} \cdot \vec{pu} = u_1 \\ \vec{pM_2} \cdot \vec{pu} = u_2 \\ \vec{pM_3} \cdot \vec{pu} = u_3 \end{cases} \quad (5)$$

in which, the vectors $\vec{pM_1}$, $\vec{pM_2}$ and $\vec{pM_3}$ are determined by $\vec{pM_1} = (x_{M1} - x_p, y_{M1} - y_p, z_{M1} - z_p)$, $\vec{pM_2} = (x_{M2} - x_p, y_{M2} - y_p, z_{M2} - z_p)$ and $\vec{pM_3} = (x_{M3} - x_p, y_{M3} - y_p, z_{M3} - z_p)$, respectively; solving the equation set (5) to obtain the value of unit vector $\vec{pu}$ of the proximal coordinate system p-uvw.

(5d) Calculating the unit vector $\vec{pv}$ of the proximal coordinate system p-uvw by using the right-hand rule, as the following equation:

$$\vec{pv} = \vec{pw} \times \vec{pu} \quad (6)$$

(5e) Repeating step (5a) to step (5d), according to the coordinates of the fourth sphere center $M_4(U_4V_4W_4)$, the fifth sphere center $M_5(U_5V_5W_5)$ and the sixth sphere center $M_6(U_6V_6W_6)$ in the distal coordinate system P-UVW, calculating the coordinate of the origin P of the distal coordinate system P-UVW in the point cloud reference coordinate system O-xyz, $P_{O\text{-}xyz}=(x_{PO}\ y_{PO}\ z_{PO})$, and determining the value of unit vectors $\vec{PU}$, $\vec{PV}$ and $\vec{PW}$ of the three coordinates axes of the distal coordinate system P-UVW in the point cloud reference coordinate system O-xyz.

(5f) Determining the position and pose of the proximal coordinate system p-uvw relative to the point cloud reference coordinate system O-xyz by using the origin coordinate $p_{O\text{-}xyz}$ and the unit vectors $\vec{pu}$, $\vec{pv}$, $\vec{pw}$; determining the position and pose of the distal coordinate system P-UVW relative to the point cloud reference coordinate system O-xyz by using the origin coordinate $P_{O\text{-}xyz}$ and the unit vectors $\vec{PU}$, $\vec{PV}$, $\vec{PW}$; and storing the spatial position and pose of the proximal and distal coordinate systems p-uvw, P-UVW into the computer system.

(6) Determining the spatial position and pose of the external fixator, including:

(6a) calculating the position of the proximal coordinate system p-uvw relative to the distal coordinate system P-UVW by using the origin p of proximal coordinate system and the origin P of distal coordinate system, determining the relative position vector $\vec{r}_{P_p}$ of the proximal fixation ring 210 and the distal fixation ring 211 as the following:

$$\vec{r}_{P_p} = p_{O\text{-}xyz} - P_{O\text{-}xyz} = (x_{pO}-x_{PO}, y_{pO}-y_{PO}, z_{pO}-z_{PO}) \quad (7)$$

(6b) calculating the relative pose of the proximal fixation ring and the distal fixation ring by using the unit vectors $\vec{pu}$, $\vec{pv}$, $\vec{pw}$ of proximal coordinate system and $\vec{PU}$, $\vec{PV}$, $\vec{PW}$ of distal coordinate system, and express the relative pose with a pose matrix $R_P^p$ of the proximal fixation ring 210 and the distal fixation ring 211 as the following:

$$R_P^p = \begin{bmatrix} \vec{pu} \cdot \vec{PU} & \vec{pv} \cdot \vec{PU} & \vec{pw} \cdot \vec{PU} \\ \vec{pu} \cdot \vec{PV} & \vec{pv} \cdot \vec{PV} & \vec{pw} \cdot \vec{PV} \\ \vec{pu} \cdot \vec{PW} & \vec{pv} \cdot \vec{PW} & \vec{pw} \cdot \vec{PW} \end{bmatrix} \quad (8)$$

(6c) determining the spatial position and pose of the external fixator according to the relative position vector $\vec{r}_{P_p}$ and pose matrix $R_P^p$ of the proximal fixation ring and the distal fixation ring;

(7) Determining the adjustment values of the external fixator for fracture reduction, including:

displaying the 3D images of the proximal bone segment 310 and the distal bone segment 311 on the screen of the computer system, translating and rotating the 3D images on the computer according to the desired fracture reduction movement, achieving the correct alignment of the proximal bone segment 310 and the distal bone segment 311 in the screen display; automatically calculating and storing, by the computer system, the translation and rotation movement values of the 3D images of the proximal bone segment 310 relative to the 3D image of the distal bone segment in the point cloud reference coordinate system O-xyz during the reduction; wherein the translation and rotation movement values of the proximal bone segment 310 relative to the distal bone segment 311 in the screen display equal to the translation and rotation adjustment value of the proximal fixation ring 210 relative to the distal fixation ring 211 during the reduction, thus the adjustment values of the external fixator for fracture reduction is determined.

(8) According to the recognized spatial position and pose of the external fixator, the adjustment values of the external fixator for fracture reduction, and by using a certain kinematics algorithm in the field of robotics, the adjustment schedule of the external fixator struts for fracture reduction is obtained. Surgeons could reduce bone fracture deformity by adjusting the struts of the external fixator according to the adjustment schedule.

The above description of the present invention is only exemplary rather than restrictive. Therefore, the embodiments of the present invention are not limited to the specific embodiments described above. If inspired by the present invention, one skilled in the art may make other changes or variations without departing from the spirit of the present invention and the scope protected by the claims, which, however, shall all fall into the protection scope of the present invention.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An automatic recognition method for spatial position and pose of a parallel external fixator, including the following steps of:

(1) installing markers, including: defining two fixation rings of the parallel external fixator as a proximal fixation ring (210) and a distal fixation ring (211); installing three markers on the proximal fixation ring and three on the distal fixation ring, wherein the six markers have the same structure and each comprise a marker ball and a marker pin shaft; the distance from a sphere center of each marker ball on the proximal fixation ring to an upper surface of the proximal fixation ring is a fixed value $h_M$; the distance from a sphere center of each marker ball on the distal fixation ring to an upper surface of the distal fixation ring is the same fixed value $h_M$; the marker balls and the marker pin shafts are made of different materials, so that the marker balls can be recognized by a common three-dimensional (hereinafter referred to as 3D) clinical imaging system, and the marker pin shafts will not be recognized;

(2) acquiring 3D images, including: 3D scanning the fracture site and the parallel external fixator with installed markers; performing threshold division and 3D reconstruction to obtain 3D images of a proximal bone segment (310), a distal bone segment (311) and six marker balls; storing the data of the 3D images in a computer system by using a 3D point cloud format, wherein the 3D point cloud format is composed of a plurality of data points to describe the surface shape of a 3D object;

(3) sphere fitting the marker balls, including:
  (a) based on the 3D point cloud data of the six marker balls and a known diameter of the marker balls, fitting the 3D point cloud of the six marker balls into six spheres by a sphere fitting algorithm;
  (b) by referring to 3D images of the proximal bone segment and the distal bone segment, specifying the correspondence relationship between the six marker balls in the 3D images and the six markers on the parallel external fixator, and then storing the correspondence relationship into the computer system;

(4) specifying installation information of the markers, including:
  (a) establishing a proximal coordinate system p-uvw attached to the proximal fixation ring and a distal coordinate system P-UVW attached to the distal fixation ring;
  (b) according to a mounting configuration among a first marker (201), a second marker (202), a third marker (203) and the proximal fixation ring, by using the structural dimensions of the proximal fixation ring, calculating the coordinates of a first sphere center of the first marker ball $M_1(u_1v_1w_1)$, a second sphere center of the second marker ball $M_2(u_2v_2w_2)$, and a third sphere center of the third marker ball $M_3(u_3v_3w_3)$ in the proximal coordinate system p-uvw, respectively; and according to a mounting configuration among a fourth marker (204), a fifth marker (205), a sixth marker (206) and the distal fixation ring (211), by using the structural dimensions of the distal fixation ring (211), calculating the coordinates of the fourth sphere center of the fourth marker ball $M_4(U_4V_4W_4)$, the fifth sphere center of the fifth marker ball $M_5(U_5V_5W_5)$, and the sixth sphere center of the sixth marker ball $M_6(U_6V_6W_6)$ in the distal coordinate system P-UVW, respectively; the sphere center coordinates of the six marker balls constitute the markers installation information of the external fixator;
  (c) inputting the markers installation information into the computer system;

(5) recognizing spatial position and pose of the coordinate systems, including:
(a) according to the plane formed by the first sphere center, second sphere center and third sphere center that is parallel to the upper surface of the proximal fixation ring, calculating a normal vector $\vec{pw}$ of the upper surface of the proximal fixation ring by the following formula, which corresponds to the axis w of the proximal coordinate system p-uvw:

$$\vec{pw} = \frac{\overrightarrow{M_1M_2} \times \overrightarrow{M_2M_3}}{|\overrightarrow{M_1M_2} \times \overrightarrow{M_2M_3}|}$$

in which, $\overrightarrow{M_1M_2}$ is a vector pointing from the first sphere center to the second sphere center in a point cloud reference coordinate system O-xyz, and $\overrightarrow{M_1M_2}=(X_{M2}-X_{M1}Y_{M2}-Y_{M1}Z_{M2}-Z_{ZM1})$; $\overrightarrow{M_2M_3}$ is a vector pointing from the second sphere center to the third sphere center in the point cloud reference coordinate system O-xyz, and $\overrightarrow{M_2M_3}=(x_{M3}-x_{m2}Y_{M3}-y_{m2}z_{m3}-z_{m2})$;

in which $x_{m1}$, $y_{m1}$, $z_{m1}$ represent coordinates of the first sphere in the point cloud reference coordinate system O-xyz, $x_{m2}$, $y_{m2}$, $z_{m2}$ represent coordinates of he second sphere in the point cloud reference coordinate system O-xyz, and $x_{m3}$, $y_{m3}$, $z_{m3}$ represent coordinates of the third sphere in the point cloud reference coordinate system O-xyz, (b) assuming the coordinates of an origin p of the proximal coordinate system p-uvw are $p_{O-xyz}=(X_{pO}Y_{pO}Z_{pO})$ in the point cloud reference coordinate system O-xyz, according to the coordinates $M_1(u_1v_1w_1)$, $M_2(u_2v_2w_2)$ and $M_3(u_3v_3w_3)$ obtained by the step (4b) in the proximal coordinate system p-uvw, calculating the coordinates of the origin p in the point cloud reference coordinate system O-xyz by solving the following distance equations:

$$\begin{cases} |\overrightarrow{pM_1}|^2 = u_1^2 + v_1^2 + w_1^2 \\ |\overrightarrow{pM_2}|^2 = u_2^2 + v_2^2 + w_2^2 \\ |\overrightarrow{pM_3}|^2 = u_3^2 + v_3^2 + w_3^2 \end{cases}$$

(c) in the point cloud reference coordinate system O-xyz, assuming the value of unit vector $\vec{pu}$ of the proximal coordinate system p-uvw is $\vec{pu}=(x_{pu}y_{pu}z_{pu})$; respectively taking the scalar products of vectors $\overrightarrow{pM_1}$, $\overrightarrow{pM_2}$ and $\overrightarrow{pM_3}$ of the first sphere center, the second sphere center and the third sphere center with the unit vector $\vec{pu}$, the outcomes are equivalent to the vector components $u_1$, $u_2$ and $u_3$ of the first sphere center, the second sphere center and the third sphere center along the axis $\vec{pu}$, expressing as the following:

$$\begin{cases} \overrightarrow{pM_1} \cdot \vec{pu} = u_1 \\ \overrightarrow{pM_2} \cdot \vec{pu} = u_2 \\ \overrightarrow{pM_3} \cdot \vec{pu} = u_3 \end{cases}$$

in which, the vectors $\overrightarrow{pM_1}$, $\overrightarrow{pM_2}$ and $\overrightarrow{pM_3}$ are determined by, $\overrightarrow{pM_1}=(x_{M1}-x_{pO}y_{m1}-y_{pO}z_{m1}-z_{pO})$, $\overrightarrow{pM_2}=(x_{M2}-x_{pO}Y_{M2}-Y_{pO}z_{M2}-z_{pO})$ and $\overrightarrow{pM_3}=(x_{m3}-x_{pO}Y_{M3}-Y_{pO}z_{M3}-z_{pO})$, respectively; solving the above equation set to determine the value of unit vector $\vec{pu}$ of the proximal coordinate system p-uvw;

(d) calculating the unit vector $\vec{pv}$ of the proximal coordinate system p-uvw according to the right-hand rule, using the following equation:

$$\vec{pv} = \vec{pw} \times \vec{pu}$$

(e) repeating step (5a) to step (5d), according to the coordinates of the fourth sphere center $M_4(U_4V_4W_4)$, the fifth sphere center $M_5(U_5V_5 W_5)$ and the sixth sphere center $M_6(U_6V_6W_6)$ in the distal coordinate system P-UVW, calculating the coordinate of an origin P of the distal coordinate system P-UVW, in the point cloud reference coordinate system O-xyz, $P_{O-xyz} = (x_{PO}Y_{PO}Z_{PO})$, and determining the value of unit vectors $\vec{PU}, \vec{PV}$ and $\vec{PW}$ of the three coordinates axes of the distal coordinate system P-UVW in the point cloud reference coordinate system O-xyz;

(f) determining the position and pose of the proximal coordinate system p-uvw relative to the point cloud reference coordinate system O-xyz by using the origin coordinate $p_{O-xyz}$ and the unit vectors $\vec{pu}, \vec{pv}, \vec{pw}$; determining the position and pose of the distal coordinate system P-UVW relative to the point cloud reference coordinate system O-xyz by using the origin coordinate $P_{O-xyz}$ and the unit vectors $\vec{PU}, \vec{PV}, \vec{PW}$; and storing the spatial position and pose of the proximal and distal coordinate systems into the computer system;

(6) determining the spatial position and pose of the external fixator, including:

(a) calculating the relative position of the proximal fixation ring and the distal fixation ring by using the origin coordinate $P_{O-xyz}$ of the proximal coordinate system and the origin coordinate $P_{O-xyz}$ of the distal coordinate system, and expressing the relative position with a position vector $\vec{r_{P_p}}$ as the following:

$$\vec{r_{P_p}} = p_{O-xyz} - P_{O-xyz} = (x_{pO} - x_{PO}, y_{pO} - y_{PO}, z_{pO} - z_{PO})$$

(b) calculating the relative pose of the proximal fixation ring and the distal fixation ring by using the unit vectors $\vec{pu}, \vec{pv}, \vec{pw}$ of the proximal coordinate system and $\vec{PU}, \vec{PV}, \vec{PW}$ of the distal coordinate system, and expressing the relative pose with a pose matrix $R_P^p$ as the following:

$$R_P^p = \begin{bmatrix} \vec{pu} \cdot \vec{PU} & \vec{pv} \cdot \vec{PU} & \vec{pw} \cdot \vec{PU} \\ \vec{pu} \cdot \vec{PV} & \vec{pv} \cdot \vec{PV} & \vec{pw} \cdot \vec{PV} \\ \vec{pu} \cdot \vec{PW} & \vec{pv} \cdot \vec{PW} & \vec{pw} \cdot \vec{PW} \end{bmatrix}$$

(c) determining the spatial position and pose of the external fixator according to the position vector $\vec{r_{P_p}}$ and pose matrix $R_P^p$ of the proximal fixation ring relative to the distal fixation ring;

(7) determining the adjustment values of the external fixator for fracture reduction, including: displaying the 3D images of the proximal bone segment and the distal bone segment on the screen of the computer system, moving the 3D images displayed on the screen according to the desired fracture reduction movement, achieving the correct alignment of the proximal bone segment and the distal bone segment in the screen display; automatically calculating and storing, by the computer system, the translation and rotation movement values of the proximal bone segment 3D image relative to the distal bone segment 3D image in the point cloud reference coordinate system O-xyz during the reduction, wherein the translation and rotation movement values of the proximal bone segment 3D image relative to the distal bone segment 3D image are equal to the translation and rotation adjustment values of the proximal fixation ring relative to the distal fixation ring during the reduction, thus the adjustment values of the external fixator for fracture reduction is determined; and (8) according to the recognized spatial position and pose of the external fixator, the adjustment values of the external fixator for fracture reduction, and by using a kinematics algorithm in the field of robotics, the adjustment schedule of the external fixator for fracture reduction is obtained; adjusting the external fixator referring to the adjustment schedule, such that the fracture reduction is achieved.

2. The method according to claim 1, wherein the three markers on the proximal fixation ring are arranged as far as possible from each other, and the three markers on the distal fixation ring are arranged as far as possible from each other.

3. The method according to claim 1, wherein the marker balls are made of stainless steel or aluminum alloy, and the marker pin shafts are made of ABS plastic or PE plastic.

4. The method according to claim 1, wherein a STL format is adopted to store the 3D images data of the proximal bone segment, the distal bone segment and the six marker balls.

5. The method according to claim 1, wherein adopting least square method to fit the 3D point cloud of each marker ball into a sphere comprising: unifying the 3D point cloud data of each marker ball into the reference coordinate system O-xyz, assuming the coordinates of the sphere center obtained by sphere fitting a marker ball point cloud as $(x_{Mk}, Y_{Mk}, Z_{Mk})$ in the reference coordinate system (where Mk represents an arbitrary $k^{th}$ marker ball), and the distance $D_i$ from the $i^{th}$ point of the $k^{th}$ marker ball's point cloud to the fitted sphere center yields the following equation:

$$D_i^2(x_{Mk}, y_{Mk}, z_{Mk}) = (x_i - x_{Mk})^2 + (y_i - y_{Mk})^2 + (z_i - z_{Mk})^2$$

in which, $x_i$, $y_i$ and $z_i$ represent coordinates of the $i^{th}$ point of the $k^{th}$ marker ball's point cloud in the reference coordinate system O-xyz;

calculating residual $s_i$ between the distance $D_i$ and the actual marker ball radius $r_M$, and further taking the sum of square residual $s_i^2$ of all the points as the following:

$$S(x_{Mk}, y_{Mk}, z_{Mk}) = \Sigma s_i^2 = \Sigma (D_i - r_m)^2$$

taking partial derivation of the sum S with respective to $x_{Mk}$, $Y_{Mk}$ and $Z_{Mk}$, a plurality of (or one) extreme values of the sum S are obtained when the partial derivation equals to 0; obtaining the minimum value of the sum S by comparing the extreme values, and the coordinates $x_{Mk}$, $Y_{Mk}$ and $Z_{Mk}$ corresponding to the minimum value is the best fitted sphere center of the chosen marker ball.

6. The method according to claim 5, wherein the three markers on the proximal fixation ring are arranged as far as possible from each other, and the three markers on the distal fixation ring are arranged as far as possible from each other.

7. The method according to claim 5, wherein the marker balls are made of stainless steel or aluminum alloy, and the marker pin shafts are made of ABS plastic or PE plastic.

8. The method according to claim 5, wherein a STL format is adopted to store the 3D images data of the proximal bone segment, the distal bone segment and the six marker balls.

* * * * *